(12) United States Patent
Xu et al.

(10) Patent No.: US 9,784,662 B2
(45) Date of Patent: Oct. 10, 2017

(54) DEVICE FOR VASCULAR HEMODYNAMIC BIONIC CELL EXPERIMENT AND METHODS FOR USING THE SAME

(71) Applicants: Chongqing University, Chongqing (CN); Chongqing University of Science and Technology, Chongqing (CN)

(72) Inventors: Zichen Xu, Chongqing (CN); Guixue Wang, Chongqing (CN); Wenfeng Xu, Chongqing (CN); Xiaoling Liao, Chongqing (CN)

(73) Assignees: Chongqing University, Chongqing (CN); Chongqing University of Science and Technology, Chongqing (CN)

( * ) Notice: Subject to any disclaimer, the term of this patent is extended or adjusted under 35 U.S.C. 154(b) by 0 days.

(21) Appl. No.: 15/272,697

(22) Filed: Sep. 22, 2016

(65) Prior Publication Data

US 2017/0089824 A1 Mar. 30, 2017

(30) Foreign Application Priority Data

Sep. 30, 2015 (CN) .......................... 2015 1 0642567

(51) Int. Cl.
*C12M 3/00* (2006.01)
*C12M 1/34* (2006.01)
(Continued)

(52) U.S. Cl.
CPC ..... *G01N 15/1436* (2013.01); *G01N 15/1404* (2013.01); *G01N 33/4915* (2013.01);
(Continued)

(58) Field of Classification Search
CPC ... C12M 41/14; C12M 41/46; G01N 15/1436; G01N 15/1404
See application file for complete search history.

(56) References Cited

U.S. PATENT DOCUMENTS

2006/0023299 A1* 2/2006 Muraki ................. C12M 41/14
359/368
2012/0034695 A1* 2/2012 Sethu ..................... C12M 29/18
435/401

FOREIGN PATENT DOCUMENTS

CN 201277972 Y 7/2009
CN 102212473 A 10/2011
(Continued)

OTHER PUBLICATIONS

Grosiman et al., (High-Throughput and High Resolution Flow Cytometry in Molded Microfluidic Devices; Anal. Chem. 2006, 78, pp. 5653-5663.*

(Continued)

*Primary Examiner* — P. Kathryn Wright
(74) *Attorney, Agent, or Firm* — Scully Scott Murphy & Presser

(57) ABSTRACT

A method of using a device for conducting a vascular hemodynamic bionic cell experiment is provided, the method comprises: firstly, experiment preparation; and secondly, experiment operation, namely, switching on a peristaltic pump, pumping a circulation liquid from a collection bottle into an independently corresponding shunting chamber of a corresponding shunting bottle through a collection bottle sampling tube of an independent chamber of a collection bottle, after shunting by the shunting chamber of the shunting bottle, the circulation liquid flowing out of a branch shunting tube flows to a corresponding flow chamber on the 1-3 flow chamber platforms placed side by side, and then converging the circulation liquid to a corresponding inde-
(Continued)

pendent chamber of the collection bottle through respective sampling tubes of the flow chamber platforms. The method provided by the present disclosure has the technical characteristics of strong practicability and low manufacturing cost, and can perform a vascular hemodynamic bionic cell experiment under multiple conditions with multiple parameters when used in combination with different models of shunting bottles and flow chamber platforms.

10 Claims, 3 Drawing Sheets

(51) Int. Cl.
    *G01N 15/14*     (2006.01)
    *G01N 33/49*     (2006.01)
    *G02B 21/36*     (2006.01)
    *G02B 21/34*     (2006.01)
    *G01N 15/00*     (2006.01)
    *G01N 15/10*     (2006.01)
    *C12M 1/00*     (2006.01)

(52) U.S. Cl.
    CPC ........... *G02B 21/34* (2013.01); *G02B 21/362* (2013.01); *C12M 41/14* (2013.01); *C12M 41/46* (2013.01); *G01N 2015/0065* (2013.01); *G01N 2015/1006* (2013.01); *G01N 2015/144* (2013.01)

(56) References Cited

FOREIGN PATENT DOCUMENTS

CN     204501097 U     7/2015
CN     105154327 A     12/2015

OTHER PUBLICATIONS

Chinese Office Action dated Sep. 29, 2016 received in Chinese Application No. 201510642676.5 together with an English-language translation.

* cited by examiner

DEVICE FOR VASCULAR HEMODYNAMIC BIONIC CELL EXPERIMENT AND METHODS FOR USING THE SAME

TECHNICAL FIELD

The present disclosure relates to a device for a biomedical experiment, and in particular to a device for vascular hemodynarmic bionic cell experiment, and a method for using the device.

BACKGROUND

A device for a vascular hemodynamic bionic cell experiment is a device for performing cytological microscope observation and study for the purpose of meeting different fluid or cell conditions. It can perform various types of experiments for simulating blood flow with different chambers of a flow chamber platform for vascular hemodynamic experiment or with different cells in the same chamber.

In biomedical engineering experiments, for comparative study experiment of multiple types of cells (such as blood cells) being separated under the stimulation of a hemodynamic force and their culturing in the same fluid environment, and for comparative study experiment of the same type of cells under different fluid environments, there is a need for a comparative experiment capable of not only ensuring experiment consistency but also meeting different conditions of cells under the influence of simulating continuous hemodynamic force of a blood vessel. In recent years, various labs are developing customized devices for cell hemodynamic experiments according to their own experimental requirements. Accordingly, according to the specific requirement in biomedical engineering research, developing a device for performing biomedical experiment and the use thereof becomes very important.

Known devices for biomedical experiments have the drawback of poor versatility, being unable to meet the requirements for simultaneous comparison under different experimental conditions, lack of effective experiment consistency, etc.

SUMMARY

In view of this, the aim of the present disclosure is to provide a device for vascular hemodynamic bionic cell experiment and a method for using the same.

To achieve this aim, the technical solution adopted by the present disclosure is as follows: a device for a vascular hemodynamic bionic cell experiment, wherein the device comprises a cabinet, a controller and a carbon dioxide gas bottle, the inside of the cabinet is partitioned into a front chamber and a rear chamber by an insulation board, a circulation fluid shunting drive system is comprised in the cabinet at one side of the front chamber, and an experiment observation system is comprised in the cabinet at the other side of said front chamber, wherein the circulation fluid shunting drive system provides circulation fluid for the experiment observation system; the circulation fluid shunting drive system comprises a shunting bottle sliding rail, a shunting bottle altitude scale, a shunting bottle, a collection bottle and a peristaltic pump; the shunting bottle sliding rail is vertically mounted on the insulation board from the top down; the shunting bottle altitude scale, parallel to the shunting bottle sliding rail, is mounted on the insulation board at one side of the shunting bottle sliding rail; the shunting bottle comprises multiple shunting chambers and is mounted on the shunting bottle sliding rail; the collection bottle comprises multiple independent chambers and the outside thereof is coated with a collection bottle heating wire, and both the collection bottle and the peristaltic pump are mounted on the bottom half of the insulation board; each independent chamber of the collection bottle is connected to a shunting chamber of the shunting bottle respectively through the multi-channel peristaltic tip of the peristaltic pump via a collection bottle sampling tube; each of the shunting chambers of the shunting bottle is connected to an inlet of an experiment observation system through the shunting tube; each fluid outlet of the experiment observation system is respectively connected to an independent chamber of the collection bottle through the sampling tube; each independent chamber of the collection bottle is connected to a shunting chamber of the shunting bottle through a shunting bottle bottom tube; a shunting bottle ventilation tube is comprised at the top of the shunting bottle; a collection bottle ventilation tube is comprised at the top of the collection bottle; a temperature control device for regulating and controlling the temperature of the front chamber is comprised in the rear chamber of the cabinet; the carbon dioxide gas bottle is connected to the shunting bottle in the cabinet through a carbon dioxide gas tube; the controller is wired to the experiment observation system, the shunting bottle sliding rail, the temperature control device and the collection bottle heating wire; all of the tubes connected with the shunting bottle are flexible tubes.

The experiment observation system comprises an illuminating lamp box, a microscope stage, a flow chamber platform, a microscope objective lens, a CCD image sensor and a microscope stand; the illuminating lamp box is mounted on the top half of the insulation board; the microscope stage is mounted on the insulation board under the illuminating lamp box; the device comprises 1-3 flow chamber platforms, all of which are comprised on the microscope stage; one end of each of the experiment flow chamber of the flow chamber platform is connected to a shunting chamber of the shunting bottle through the shunting tubes, and the other end is connected to an independent chamber of the collection bottle through the sampling tubes; the microscope objective lens is mounted on the microscope stand under the microscope stage; the CCD image sensor is mounted on the microscope stand under the microscope objective lens; the microscope stand is mounted on the insulation board under the CCD image sensor; the controller is wired to the microscope objective lens and the CCD image sensor.

The insulation board is provided with at least two circulation air filtering ports from the top down; the temperature control device comprises a heating motor fixed in the middle of the insulation board and two draught fans each fixed respectively at one of the two circulation air filtering ports on the insulation board; the heating motor and the two draught fans are connected through an upper air duct and a lower air duct, respectively.

Further, in some embodiments, 1 type of circulation liquid, 1 shunting bottle and 1 collection bottle is used to provide circulation liquid for the chambers of 3 flow chamber platforms; or 2 different types of circulation liquid, 2 drift bottles and 2 collection bottles are used to provide 2 different types of circulation liquid for the chambers of 3 flow chamber platforms; and when a long-term fluid experiment for living cells is performed, a flow chamber constant-temperature box is additionally comprised by the flow chamber platform.

Further, the outside of the flow chamber platform is configured to comprise a flow chamber constant-temperature box.

Further, the top of the front chamber of the cabinet is configured to comprise the ultraviolet lamp which is wired to the controller.

Further, the top of the front chamber of the cabinet is configured to comprise a temperature-humidity sensor which is wired to the controller.

Further, the cabinet is hermetic and thermal-insulated.

Further, the entire front surface of the cabinet is configured to be a transparent door.

Further, the entire back surface of the cabinet is configured to be a transparent door comprising an upper and a lower air inlet with a filter net.

Further, the device comprises 1-3 shunting bottle sliding rails, each of which is equipped with a shunting bottle, and the number of the collection bottles is the same as that of the shunting bottles.

In another aspect, the present disclosure provides a method of using a device for a vascular hemodynamic bionic cell experiment, wherein the device for the vascular hemodynamic bionic cell experiment comprises a cabinet, a controller and a carbon dioxide gas bottle, the inside of the cabinet is partitioned into a front chamber and a rear chamber by an insulation board, a circulation fluid shunting drive system is comprised in the cabinet at one side of the front chamber, and an experiment observation system is comprised in the cabinet at the other side of said front chamber, wherein the circulation fluid shunting drive system provides circulation fluid for the experiment observation system; the circulation fluid shunting drive system comprises a shunting bottle sliding rail, a shunting bottle altitude scale, a shunting bottle, a collection bottle and a peristaltic pump; the shunting bottle sliding rail is vertically mounted on the insulation board from the top down; the shunting bottle altitude scale, parallel to the shunting bottle sliding rail, is mounted on the insulation board at one side of the shunting bottle sliding rail; the shunting bottle comprises multiple shunting chambers and is mounted on the shunting bottle sliding rail; the collection bottle comprises multiple independent chambers and the outside thereof is coated with a collection bottle heating wire, and both the collection bottle and the peristaltic pump are mounted on the bottom half of the insulation board; each independent chamber of the collection bottle is connected to a shunting chamber of the shunting bottle respectively through the multi-channel peristaltic tip of the peristaltic pump via a collection bottle sampling tube; each of the shunting chambers of the shunting bottle is connected to an inlet of an experiment observation system through the shunting tube; each fluid outlet of the experiment observation system is respectively connected to an independent chamber of the collection bottle through the sampling tube; each independent chamber of the collection bottle is connected to a shunting chamber of the shunting bottle through a shunting bottle bottom tube; a shunting bottle ventilation tube is comprised at the top of the shunting bottle; a collection bottle ventilation tube is comprised at the top of the collection bottle; a temperature control device for regulating and controlling the temperature of the front chamber is comprised in the rear chamber of the cabinet; the carbon dioxide gas bottle is connected to the shunting bottle in the cabinet through a carbon dioxide gas tube; the controller is wired to the experiment observation system, the shunting bottle sliding rail, the temperature control device and the collection bottle heating wire; all of the tubes connected with the shunting bottle are flexible tubes.

The experiment observation system comprises an illuminating lamp box, a microscope stage, a flow chamber platform, a microscope objective lens, a CCD image sensor and a microscope stand; the illuminating lamp box is mounted on the top half of the insulation board; the microscope stage is mounted on the insulation board under the illuminating lamp box; the device comprises 1-3 flow chamber platforms, all of which are comprised on the microscope stage; one end of each of the experiment flow chamber of the flow chamber platform is connected to a shunting chamber of the shunting bottle through the shunting tubes, and the other end is connected to an independent chamber of the collection bottle through the sampling tubes; the microscope objective lens is mounted on the microscope stand under the microscope stage; the CCD image sensor is mounted on the microscope stand under the microscope objective lens; the microscope stand is mounted on the insulation board under the CCD image sensor; the controller is wired to the microscope objective lens and the CCD image sensor.

The insulation board is provided with at least two circulation air filtering ports from the top down; the temperature control device comprises a heating motor fixed in the middle of the insulation board and two draught fans each fixed respectively at one of the two circulation air filtering ports on the insulation board; the heating motor and the two draught fans are connected through an upper air duct and a lower air duct, respectively.

The method comprises the steps of:

Firstly, experiment preparation, namely, preparing 1-3 flow chamber platforms containing living cells, placing the flow chamber platforms on the microscope stage in a matching manner, fixing the flow chamber platforms, and connecting all tubes to form an independent loop; switching on the controller to control the temperature of circulation air in the cabinet to be constant at 37° C., opening the carbon dioxide gas bottle so as to introduce carbon dioxide into the shunting bottle; pouring a circulation liquid for the experiment into 1-3 collection bottles, turning on the collection bottle heating wire for heating, maintaining the temperature to be constant at 37° C., and controlling the shunting bottle to be fixed at a height required by the experiment; and turning on an ultraviolet lamp to keep the temperature constant for 30 min to 60 min.

Secondly, experiment operation, namely, switching on a peristaltic pump, pumping the circulation liquid from the collection bottle into a corresponding shunting chamber of a corresponding shunting bottle through the collection bottle sampling tube of an independent chamber of the collection bottle passing through the pump tip of the peristaltic pump; after shunting by the shunting chambers of the shunting bottle, the circulation liquid flowing out of a branch shunting tube flows into a corresponding flow chamber on the 1-3 flow chamber platforms placed side by side, and then converging the circulation liquid into a corresponding independent chamber of the collection bottle through respective sampling tubes of a flow chamber platform; the liquid remained in the shunting chambers of the shunting bottle flows back to a corresponding chamber of the collection bottle through the shunting bottle bottom tubes of the shunting chambers; maintaining the flow rate constant, switching on a microscope to perform a living cell observation experiment for each flow chamber; and collecting image data with the CCD.

The device and the method provided by the present disclosure has the technical characteristics of strong practicability and low manufacturing cost, and can perform a vascular hemodynamic bionic cell experiment under multiple conditions with multiple parameters when used in combination with different models of shunting bottles and flow chamber platforms; and the method provided by the present disclosure is flexible and convenient to use and has better versatility. One device can simultaneously perform multiple living cell fluid experiments under different conditions, with fast speed and high efficiency.

BRIEF DESCRIPTION OF THE DRAWINGS

The present disclosure will be further described hereinafter with reference to drawings.

In the figures: 1, sampling tube; 2, collection bottle; 3, cabinet; 4, collection bottle sampling tube; 5, controller; 6, peristaltic pump; 7, carbon dioxide gas bottle; 8, collection bottle heating wire; 9, collection bottle ventilation tube; 10, shunting bottle bottom tube; 11, shunting bottle; 12, carbon dioxide gas tube; 13, shunting bottle sliding rail; 14, shunting bottle altitude scale; 15, shunting bottle ventilation tube; 16, shunting tube; 17, illuminating lamp box; 18, flow chamber platform; 19, microscope stage; 20, CCD image sensor; 21, microscope stand; 22, flow chamber constant-temperature box; 23, microscope objective lens; 24, circulation air filtering port; 25, ultraviolet lamp; 26, insulation board; 27, draught fan; 28, air duct; 29, heating motor; 30, air inlet with a filter net; and 31, temperature-humidity sensor.

DETAILED DESCRIPTION

Figure 1:
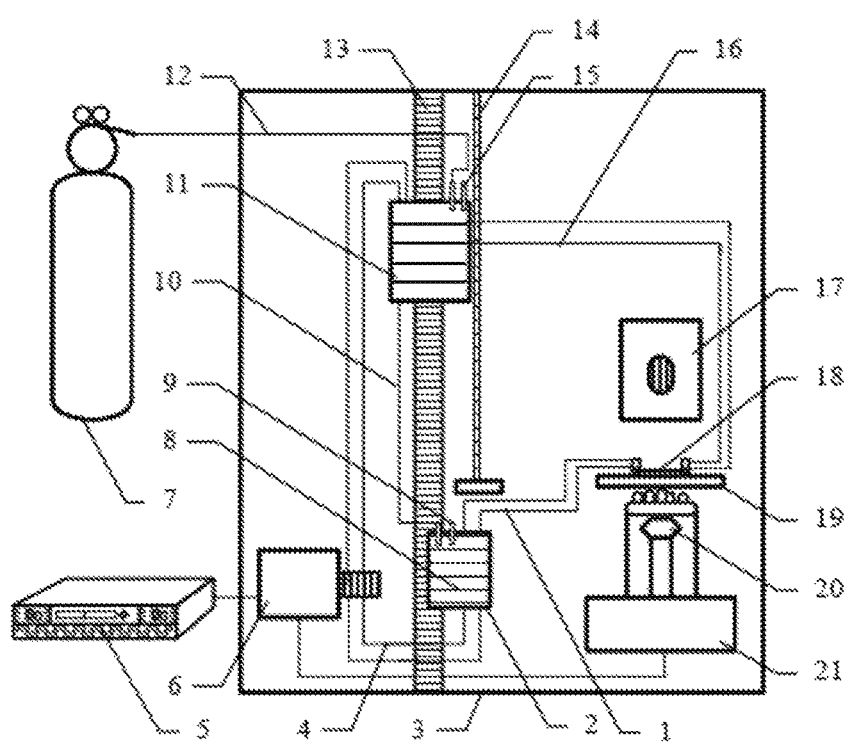
FIG. 1 is a schematic front view of the device provided by the present disclosure.
Figure 2:
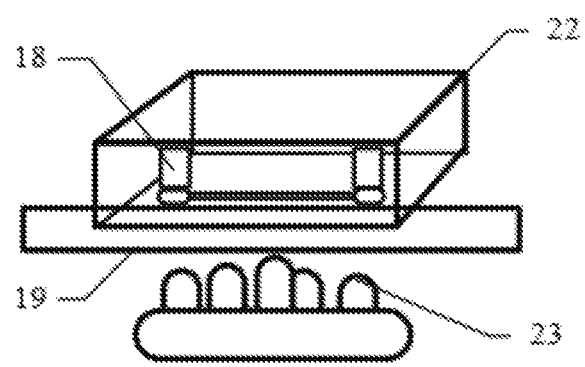
FIG. 2 is a schematic diagram of the device provided by the present disclosure additionally comprising a flow chamber constant-temperature box.
Figure 3:
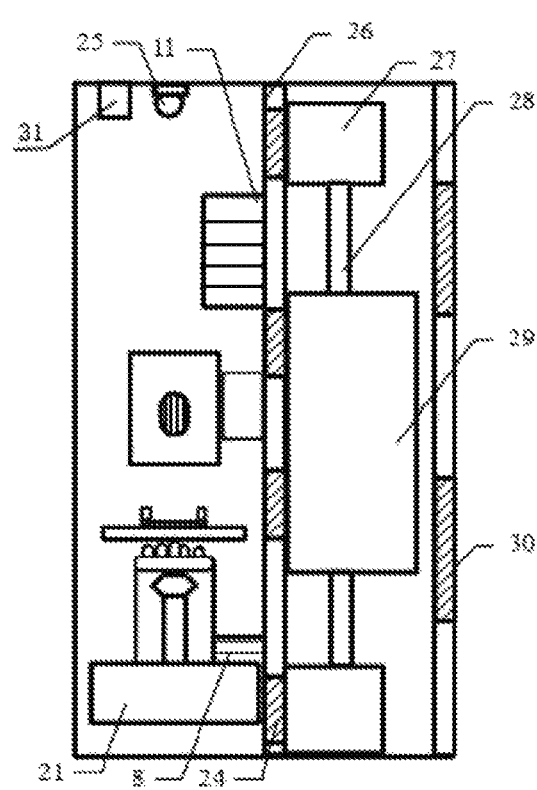
FIG. 3 is a schematic diagram of a right view of the device provided by the present disclosure.

As shown in FIG. 1 to FIG. 3, a device for conducting vascular hemodynamic bionic cell experiment and a method for using the same are provided, the device includes a cabinet 3, a controller 5 and a carbon dioxide gas bottle 7; the inside of the cabinet 3 is partitioned into a front chamber and a rear chamber by an insulation board 26, a circulation fluid shunting drive system is comprised at one side of the front chamber of the cabinet, and an experiment observation system is comprised at the other side; the circulation fluid shunting drive system provides circulation fluid for the experiment observation system; the circulation fluid shunting drive system includes a shunting bottle sliding rail 13, a shunting bottle altitude scale 14, a shunting bottle 11, a collection bottle 2 and a peristaltic pump 6; the shunting bottle sliding rail 13 is vertically mounted on the insulation board 26 from the top down; the shunting bottle altitude scale 14, parallel to the shunting bottle sliding rail 13, is mounted on the insulation board 26 at one side of the shunting bottle sliding rail 13; the shunting bottle 11 includes multiple shunting chambers and is mounted on the shunting sliding rail 13; the collection bottle 2 includes multiple independent chambers and the outside thereof is coated with collection bottle heating wires 8; both the collection bottle 2 and the peristaltic pump 6 are mounted on the bottom half of the insulation board 26; each of the independent chambers of the collection bottle 2 respectively passes through the multi-channel peristaltic tip of the peristaltic pump 6 via a collection bottle sampling tube 4 to be connected to a shunting chamber of the shunting bottle 11; each of the shunting chambers of the shunting bottle 11 is connected to a fluid inlet of an experiment observation system through a shunting tube 16; a fluid outlet of the experiment observation system is connected to a corresponding independent chambers of the collection bottle 2 through a sampling tube 1; each of the independent chambers of the collection bottle 2 is connected to a shunting chamber of the shunting bottle 11 through a shunting bottle bottom tube 10 of the shunting bottle 11; the top of the shunting bottle 11 is configured to comprise a shunting bottle ventilation tube 15; the top of the collection bottle 2 is configured to comprise a collection bottle ventilation tube 9; a temperature control device for regulating and controlling the temperature of the front chamber is comprised in the rear chamber of the cabinet; the carbon dioxide gas bottle 7 is connected to the shunting bottle 11 in the cabinet 3 through a carbon dioxide gas tribe 12; the controller 5 is wired to the experiment observation system, the shunting bottle sliding rail 13, the temperature control device and the collection bottle heating wire 8; and all of the tubes connected with the shunting bottle 11 are flexible tubes.

The experiment observation system includes an illuminating lamp box 17, a microscope stage 19, a flow chamber platform 18, a microscope objective lens 23, a CCD image sensor 20 and a microscope stand 21; the illuminating lamp box 17 is mounted on the top half of the insulation board 26; the microscope stage 19 is mounted on the insulation board 26 under the illuminating lamp box 17; 1-3 flow chamber platforms 18 are comprised on the microscope stage 19; one end of each of the experiment flow chamber of the flow chamber platform 18 is connected to a shunting chamber of the shunting bottle 11 through the shunting tubes 16, and the other end is connected to an independent chamber of the collection bottle 2 through the sampling tubes 1; the microscope objective lens 23 is mounted on the microscope stand 21 under the microscope stage 19; the CCD image sensor 20 is mounted on the microscope stand 21 under the microscope objective lens 23; the microscope stand 21 is mounted on the insulation board 26 under the CCD image sensor 20; and the controller 5 is wired to the microscope objective lens 23 and the CCD image sensor 20.

The insulation board 26 is provided with at least two circulation air filtering ports from the top down; the temperature control device comprises a heating motor 29 fixed in the middle of the insulation board 26 and two draught fans 27 each fixed respectively at one of the two circulation air filtering ports on the insulation board 26; and the heating motor 29 and the two draught fans 27 are connected through an upper air duct and a lower air duct, respectively.

The method includes the steps of:

firstly, experiment preparation, namely, preparing 1-3 flow chamber platforms 18 containing living cells, placing the flow chamber platforms 18 on the microscope stage 19 in a matching manner, fixing the flow chamber platforms, and connecting all tubes to form an independent loop; switching on the controller 5 to control the temperature of circulation air in the cabinet 3 to be constant at 37° C., and opening the carbon dioxide gas bottle 7 so as to introduce carbon dioxide into the shunting bottle 11; pouring a circulation liquid for the experiment into 1-3 collection bottles 2, turning on the collection bottle heating wires 8 for heating, maintaining the temperature to be constant at 37° C., and controlling the shunting bottle 11 to be fixed at a height required by the experiment; and turning on an ultraviolet lamp 25 to keep the temperature constant for 30 min to 60 min;

secondly, experiment operation, namely, switching on a peristaltic pump 6, pumping the circulation liquid from the collection bottle 2 into a corresponding shunting chamber of a corresponding shunting bottle 11 through the collection bottle sampling tube 4 of an independent chamber of the collection bottle 2 passing through the pump tip of the peristaltic pump 6; after shunting by the shunting chambers of the shunting bottle 2, the circulation liquid flowing out of a branch shunting tube 16 flows into a corresponding flow chamber on the 1-3 flow chamber platforms 18 placed side by side, and then converging the circulation liquid into a corresponding independent chamber of the collection bottle 2 through respective sampling tubes 1 of a flow chamber platform 18; the liquid remained in the shunting chambers of the shunting bottle 11 flows back to a corresponding chamber of the collection bottle 2 through the shunting bottle bottom tubes 10 of the shunting bottles 11; maintaining the flow rate constant, switching on a microscope to perform a living cell observation experiment for each flow chamber; and collecting image data with the CCD.

As a further optimization of the present disclosure, 1 type of circulation liquid, 1 shunting bottle 11 and 1 collection bottle 2 may be used to provide circulation liquid for the chambers of 3 flow chamber platforms 18; or 2 different types of circulation liquid, 2 drift bottles and collection bottle 2 are used to provide 2 different types of circulation liquid for the chambers 3 flow chamber platforms 18; and when a long-term fluid experiment for living cells is performed, a flow chamber constant-temperature box 22 is additionally comprised by the flow chamber platform 18.

As a further optimization of the present disclosure, the experiment observation system includes an illuminating lamp box 17, a microscope stage 19, a flow chamber platform 18, a microscope objective lens 23, a CCD image sensor 20 and a microscope stand 21; the illuminating lamp box 17 is mounted on the upper half part of the insulation board 26; the microscope stage 19 is mounted on the insulation board 26 under the illuminating lamp box 17; 1-3 flow chamber platforms 18 are comprised on the microscope stage 19; one end of each of the experiment flow chamber of the flow chamber platform 18 is connected to a shunting chamber of the shunting bottle 11 through the shunting tubes 16, and the other end is connected to an independent chamber of the collection bottle 2 through the sampling tubes 1; the microscope objective lens 23 is mounted on the microscope stand 21 under the microscope stage 19; the CCD image sensor 20 is mounted on the microscope stand 21 under the microscope objective lens 23; the microscope stand 21 is mounted on the insulation board 26 under the CCD image sensor 20; and the controller is wired to the microscope objective lens 23 and the CCD image sensor 20. The illuminating lamp box 17 provides light source for the experiment observation system, the flow chamber platform 18 is placed on the microscope stage 19, the microscope objective lens 23 is used for observing the flow chamber platform 18, the CCD image sensor 20 is used for imaging, and the microscope stand 21 is used for supporting the microscope objective lens 23 and the CCD image sensor 20. The controller 5 can control the microscope objective lens 23 and the CCD image sensor 20. The outside of the flow chamber platform 18 is provided with the flow chamber constant-temperature box 22. This design is for meeting the requirement of long-term fluid experiment for living cells to guarantee a proper temperature for living cells. The insulation board 26 is provided with at least two circulation air filtering ports 24 from the top down, the temperature control device includes a heating motor 29 fixed in the middle of the insulation board 26 and two draught fans 27 each fixed respectively at one of the two circulation air filtering ports 24 on the insulation board; and the heating motor 29 and the two draught fans 27 are connected through an upper air duct and a lower air duct 28, respectively. This design is mainly for controlling the environment temperature of the front chamber of the cabinet 3. The top of the front chamber of the cabinet 3 is configured to comprise the ultraviolet lamp 25, which is wired to the controller 5. The ultraviolet lamp 25 is used for sterilizing the cabinet 3 to ensure that the cell experiment is not polluted. The top of the front chamber of the cabinet 3 is configured to comprise the temperature-humidity sensor 31, which is wired to the controller 5. The temperature-humidity sensor 31 provides data for controlling the temperature and humidity of the cabinet 3, and the controller 5 controls on and off of the heating motor 29 via feedback data. The cabinet 3 is hermetic and thermal-insulated. This design makes the temperature in the entire cabinet 3 more stable and controllable. The entire front surface of the cabinet 3 is set as a transparent door for the purpose of conveniently changing and maintaining components and also conveniently observing the circulation of fluid. The entire back surface of the cabinet 3 is set as a transparent door which comprises an upper and a lower air inlet 30 with filtering net for the purpose of conveniently changing and maintaining components, conveniently observing the circulation of fluid and conveniently ventilating the cabinet 3. The number of the shunting bottle sliding rail 13 is 1-3, each of the shunting bottle sliding rails 13 is equipped with the shunting bottle 11, and the number of the collection bottle 2 is the same as that of the shunting bottle 11. This design can meet the requirements of different experiment conditions.

Finally, it should be noted that the above embodiments are only used to illustrate the technical solution of the present disclosure but not to be construed as limitation; although the present disclosure is described in detail with reference to preferred embodiments, it should be understood for those of ordinary skill in the art that modifications or equivalent substitutions can be made to the technical solution of the present disclosure without departing from the spirit and scope of the technical solution of the present disclosure, which are all included in the scope of the claims of the present disclosure.

The invention claimed is:

1. A device for vascular hemodynamic bionic cell experiment, wherein the device comprises a cabinet, a controller and a carbon dioxide gas bottle, the inside of the cabinet is partitioned into a front chamber and a rear chamber by an insulation board, a circulation fluid shunting drive system is comprised in the cabinet at one side of the front chamber, and an experiment observation system is comprised in the cabinet at the other side of said front chamber, wherein the circulation fluid shunting drive system provides circulation fluid for the experiment observation system; the circulation fluid shunting drive system comprises a shunting bottle sliding rail, a shunting bottle altitude scale, a shunting bottle, a collection bottle and a peristaltic pump; the shunting bottle sliding rail is vertically mounted on the insulation board from the top down; the shunting bottle altitude scale, parallel to the shunting bottle sliding rail, is mounted on the insulation board at one side of the shunting bottle sliding rail; the shunting bottle comprises multiple shunting chambers and is mounted on the shunting bottle sliding rail; the collection bottle comprises multiple independent chambers and the outside thereof is coated with a collection bottle heating wire, and both the collection bottle and the peristaltic pump are mounted on the bottom half of the insulation board; each independent chamber of the collection bottle is connected to a shunting chamber of the shunting bottle respectively through the multichannel peristaltic tip of the peristaltic pump via a collection bottle sampling tube; each of the shunting chambers of the shunting bottle is connected to an inlet of an experiment observation system through the shunting tube; each fluid outlet of the experiment observation system is respectively connected to an independent chamber of the collection bottle through the sampling tube; each independent chamber of the collection bottle is connected to a shunting chamber of the shunting bottle through a shunting bottle bottom tube; a shunting bottle ventilation tube is comprised at the top of the shunting bottle; a collection bottle ventilation tube is comprised at the top of the collection bottle; a temperature control device for regulating and controlling the temperature of the front chamber is comprised in the rear chamber of the cabinet; the carbon dioxide gas bottle is connected to the shunting bottle in the cabinet through a carbon dioxide gas tube; the controller is wired to the experiment observation system, the shunting bottle sliding rail, the temperature control device and the collection bottle heating wire; all of the tubes connected with the shunting bottle are flexible tubes; the experiment observation system comprises an illuminating lamp box, a microscope stage, a flow chamber platform, a microscope objective lens, a CCD image sensor and a microscope stand; the illuminating lamp box is mounted on the top half of the insulation board; the microscope stage is mounted on the insulation board under the illuminating lamp box; the device comprises a plurality of flow chamber platforms, all of which are comprised on the microscope stage; one end of each of the experiment flow chamber of the flow chamber platform is connected to a shunting chamber of the shunting bottle through the shunting tubes, and the other end is connected to an independent chamber of the collection bottle through the sampling tubes; the microscope objective lens is mounted on the microscope stand under the microscope stage; the CCD image sensor is mounted on the microscope stand under the microscope objective lens; the microscope stand is mounted on the insulation board under the CCD image sensor; the controller is wired to the microscope objective lens and the CCD image sensor; the insulation board is provided with at least two circulation air filtering ports from the top down; the temperature control device comprises a heating motor fixed in the middle of the insulation board and two draught fans each fixed respectively at one of the two circulation air filtering ports on the insulation board; and the heating motor and the two draught fans are connected through an upper air duct and a lower air duct, respectively.

2. The device according to claim 1, wherein 1 type of circulation liquid, 1 shunting bottle and 1 collection bottle is used to provide circulation liquid for the chambers of 3 flow chamber platforms; or 2 different types of circulation liquid, 2 drift bottles and 2 collection bottles are used to provide 2 different types of circulation liquid for the chambers of 3 flow chamber platforms; and when a fluid experiment for living cells is performed, a flow chamber constant-temperature box is additionally comprised by the flow chamber platform.

3. The device according to claim 2, wherein the outside of each flow chamber platform is configured to comprise a flow chamber constant-temperature box.

4. The device according to claim 1, wherein the top of the front chamber of the cabinet is configured to comprise the ultraviolet lamp which is wired to the controller.

5. The device according to claim 1, wherein the top of the front chamber of the cabinet is configured to comprise a temperature-humidity sensor which is wired to the controller.

6. The device according to claim 1, wherein the cabinet is hermetic and heat-insulated.

7. The device according to claim 1, wherein the entire front surface of the cabinet is configured to be a transparent door.

8. The device according to claim 1, wherein the entire back surface of the cabinet is configured to be a transparent door comprising an upper and a lower air inlet with a filter net.

9. The device according to claim 1, wherein the device comprises 1-3 shunting bottle sliding rails, each of which is equipped with a shunting bottle, and the number of the collection bottles is the same as that of the shunting bottles.

10. A method of using a device for a vascular hemodynamic bionic cell experiment, wherein the device for the vascular hemodynamic bionic cell experiment comprises a cabinet, a controller and a carbon dioxide gas bottle, the inside of the cabinet is partitioned into a front chamber and a rear chamber by an insulation board, a circulation fluid shunting drive system is comprised in the cabinet at one side of the front chamber, and an experiment observation system is comprised in the cabinet at the other side of said front chamber, wherein the circulation fluid shunting drive system provides circulation fluid for the experiment observation system; the circulation fluid shunting drive system comprises a shunting bottle sliding rail, a shunting bottle altitude scale, a shunting bottle, a collection bottle and a peristaltic pump; the shunting bottle sliding rail is vertically mounted on the insulation board from the top down; the shunting bottle altitude scale, parallel to the shunting bottle sliding rail, is mounted on the insulation board at one side of the shunting bottle sliding rail; the shunting bottle comprises multiple shunting chambers and is mounted on the shunting bottle sliding rail; the collection bottle comprises multiple independent chambers and the outside thereof is coated with a collection bottle heating wire, and both the collection bottle and the peristaltic pump are mounted on the bottom half of the insulation board; each independent chamber of the collection bottle is connected to a shunting chamber of the shunting bottle respectively through the multi-channel peristaltic tip of the peristaltic pump via a collection bottle sampling tube; each of the shunting chambers of the shunting bottle is connected to an inlet of an experiment observation system through the shunting tube; each fluid outlet of the experiment observation system is respectively connected to an independent chamber of the collection bottle through the sampling tube; each independent chamber of the collection bottle is connected to a shunting chamber of the shunting bottle through a shunting bottle bottom tube; a shunting bottle ventilation tube is comprised at the top of the shunting bottle; a collection bottle ventilation tube is comprised at the top of the collection bottle; a temperature control device for regulating and controlling the temperature of the front chamber is comprised in the rear chamber of the cabinet; the carbon dioxide gas bottle is connected to the shunting bottle in the cabinet through a carbon dioxide gas tube; the controller is wired to the experiment observation system, the shunting bottle sliding rail, the temperature control device and the collection bottle heating wire; all of the tubes connected with the shunting bottle are flexible tubes; the experiment observation system comprises an illuminating lamp box, a microscope stage, a flow chamber platform, a microscope objective lens, a CCD image sensor and a microscope stand; the illuminating lamp box is mounted on the top half of the insulation board; the microscope stage is mounted on the insulation board under the illuminating lamp box; the device comprises a plurality of flow chamber platforms, all of which are comprised on the microscope stage; one end of each of the experiment flow chamber of the flow chamber platform is connected to a shunting chamber of the shunting bottle through the shunting tubes, and the other end is connected to an independent chamber of the collection bottle through the sampling tubes; the microscope objective lens is mounted on the microscope stand under the microscope stage; the CCD image sensor is mounted on the microscope stand under the microscope objective lens: the microscope stand is mounted on the insulation board under the CCD image sensor; the controller is wired to the microscope objective lens and the CCD image sensor; the insulation board is provided with at least two circulation air filtering ports from the top down; the temperature control device comprises a heating motor fixed in the middle of the insulation board and two draught fans each fixed respectively at one of the two circulation air filtering ports on the insulation board; the heating motor and the two draught fans are connected through an upper air duct and a lower air duct, respectively; the method comprises the steps of:

firstly, experiment preparation, namely, preparing the plurality of flow chamber platforms containing living cells, placing the flow chamber platforms on the microscope stage in a matching manner, fixing the flow chamber platforms, and connecting all tubes to form an independent loop; switching on the controller to control the temperature of circulation air in the cabinet to be constant at 37° C., opening the carbon dioxide gas bottle so as to introduce carbon dioxide into the shunting bottle; pouring a circulation liquid for the experiment into a plurality of collection bottles, turning on the collection bottle heating wire for heating, maintaining the temperature to be constant at 37° C., and controlling the shunting bottle to be fixed at a height required by the experiment; and turning on an ultraviolet lamp to keep the temperature constant for 30 min to 60 min;

secondly, experiment operation, namely, switching on a peristaltic pump, pumping the circulation liquid from the collection bottle into a corresponding shunting chamber of a corresponding shunting bottle through the collection bottle sampling tube of an independent chamber of the collection bottle passing through the pump tip of the peristaltic pump; after shunting by the shunting chambers of the shunting bottle, the circulation liquid flowing out of a branch shunting tube flows into a corresponding flow chamber on the plurality of flow chamber platforms placed side by side, and then converging the circulation liquid into a corresponding independent chamber of the collection bottle through respective sampling tubes of a flow chamber platform; the liquid remained in the shunting chambers of the shunting bottle flows back to a corresponding chamber of the collection bottle through the shunting bottle bottom tubes of the shunting chambers; maintaining the flow rate constant, switching on a microscope to perform a living cell observation experiment for each flow chamber; and collecting image data with the CCD.

\* \* \* \* \*